US006506801B1

(12) United States Patent
Yee et al.

(10) Patent No.: US 6,506,801 B1
(45) Date of Patent: Jan. 14, 2003

(54) METHODS OF TREATING ANOSMIA AND REPOPULATING OLFACTORY NERVES WITH RETINOIDS

(75) Inventors: Karen K. Yee, Philadelphia, PA (US); Nancy E. Rawson, Marlton, NJ (US)

(73) Assignee: Monell Chemical Senses Center, Philadelphia, PA (US)

( * ) Notice: Subject to any disclaimer, the term of this patent is extended or adjusted under 35 U.S.C. 154(b) by 0 days.

(21) Appl. No.: 09/969,421

(22) Filed: Oct. 2, 2001

Related U.S. Application Data
(60) Provisional application No. 60/237,900, filed on Oct. 4, 2000.

(51) Int. Cl.$^7$ ................................................ A61K 31/07
(52) U.S. Cl. ...................................................... 514/725
(58) Field of Search ......................................... 514/725

(56) References Cited

PUBLICATIONS

Roydhouse, N., New Zealand Medical Journal, 101(849), 465 (Jul. 13, 1988).*
Aderoju, A.O. et al., "Vitamin A in olfactory mucosa and its effect on gene expression in neurons in vivo", *Amer Chem Soc. Abstracts*, 2000, Abstract 195.
Ahmad, O. et al., "Expression of cellular retinoic acid binding proteins in mature rat olfactory epithelium", *Amer. Chem Soc Abstracts*, 2000, Abstract 194.
Anchan, R.M, et al., "Disruption of local retinoid–mediated gene expression accompanies abnormal development in the mammalian olfactory pathway", *J. Comp. Neurol.*, 1997, 379, 171–184.
Butler,et al., ". . . bulbectomized rats with new olfactory– . . . connections are anosmic" Neurosci. Lett., 1984, 48, 247–254.
Cancalon, P. et al., "Study of regeneration in the garfish olfactory nerve", *J. Cell Biol.*, 1980, 84, 779–794.
Chiang, M.Y. et al., "An essential role for retinoid receptors RARβ and RXRy in long term potentiation and depression", *Neuron*, 1999, 21, 1353–1361.
Corcoran, J. et al., "Nerve growth factor acts via retinoic acid synthesis to stimulate neurite outgrowth", *Nat Neurosci.*, 1999, 2, 307–308.
Costanzo, R.M. "Neural regeneration and functional reconnection following olfactory nerve transection in hamster", *Brain. Res.*, 1985, 361, 258–266.
Cummings, D.M. et al., "Pattern of olfactory bulb innervation returns after recovery from reversible peripheral deafferentation" *J. Comp. Neurol.*, 2000, 421, 362–373.
Duncan, R.B. et al., "Treatment of uncomplicated anosmia by vitamin A", *Archives of Otolaryngology*, 1962, 75, 116–124.
Gheusi, G. et al., "Importance of newly generated neurons in the adult olfactory bulb for odor discrmination", *Proc. Natl. Acad. Sci. USA*, 2000, 97, 1823–1828.

Graziadei, P.P.C. et al., "Neuronal regeneration in frog olfacotry system", *J. Cell Biol.*, 1973, 59, 525–30.
Graziadei & Graziadei, "The olfactory system: a model for the study of neurogenesis and axon regeneration in mammals". In C.W. Cotman (ed), Neuronal Plasticity, New York, Raven Press, 1978, pp 131–153.
Graziadei, G.A.M. et al., "Neuroegenesis and neuron regeneration in the olfactory system of mammals. II. Degeneration and reconstitution of the olfactory sensory neurons after axotomy", *Jrl. of Neurocytology.*, 1979, 8, 197–213.
Gustafson, A–L et al., "CRBP1 and CRABP I localisation during olfactory nerve development", *Dev. Brain Res.*, 1999, 114, 121–126.
Harding, J.W. et al., "Denervation of the primary olfactory pathway in mice. V. Long–term effect of intranasal ZnSO4 irrigation on behavior, biochemistry and morphology", *Brain Res.*, 1978, 140, 271–285.
Hoag, W.G. et al., Biology of a laboratory mouse, E.L. Green(Ed.), Dover Publications Inc, New York, 2000, 39–43.
LaMantia, A.S. et al., "Retinoic acid induction and regional differentiation prefigure olfactory pathway formation in the mammalian forebrain", *Neuron*, 1993, 10, 1035–1048.
Oley, N. et al., "Recovery of structure and function following transection of the primary olfactory nerves in pigeons", *J. Comp. Physiol. Psychol.*, 1975, 88, 477–495.
*Remington's Pharmaceutical Sciences* (Mack Pub. Co., Easton, PA, 1980).
Setzer, A.K. et al., "Odor detection in rats with 3–methylindole–induced reduction of sensory input", *Physiol. Behav.*, 1998, 65, 489–496.
Simmons, P.A. et al., "Physiological activity of newly differentiated olfactory receptor neurons correlated with morphological recovery from olfactory nerve section in the salamander", *Jrl. of Neurophysiology*, 1981, 45, 529–549.
Suzuki, Y. et al., "Colchicine–induced cell death and proliferation in the olfactory epithelium and vomeronasal organ of the mouse" *Anat. Embryol. (Berl)*, 1998, 198, 43–51.
Thacher, S.M. et al., "Therapeutic applications for ligands of retinoid receptors" *Curr. Pharm. Design*, 2000, 6, 25–58.
Whitesides, J. et al., "Retinoid signaling distinguishes a subpopulation of olfactory receptor neurons in the developing and adult mouse", *J. Comp. Neurol.*, 1998, 394, 445–461.
Yee, K.K. et al., "Restoration of olfactory mediated behavior after olfactory bulb deafferentation", *Physiol. Behav.*, 1995, 58, 1–10.
Youngentob, S.L. et al., "Odorant threshold following methyl bromide–induced lesions of the olfactory epithelium", *Physiol. Behav.*, 1997, 62, 241–1252.

(List continued on next page.)

*Primary Examiner*—Phyllis G. Spivack
(74) *Attorney, Agent, or Firm*—Woodcock Washburn LLP

(57) ABSTRACT

The present invention provides methods of treating complicated anosmia in a mammal, methods of enhancing the rate of olfactory nerve recovery in a mammal, and methods of enhancing nerve regeneration in a mammal by administering an effective amount of a retinoid compound to the mammal.

17 Claims, 2 Drawing Sheets

OTHER PUBLICATIONS

Zhang, Q–Y, "Retinoic acid biosynthetic activity and retinoid receptors in the olfactory mucosa of adult mice" *Biochem Biophys Res Commun.*, 1999, 256, 346–351.

Monell Chemical Senses Center, Executive Meeting & Dinner, Program May 4, 2000.

Etchamendy, N. et al., "Alleviation of a selective age–related relational memory deficit in mice pharmacologically induced normalization of brain retinoid signaling", *The Journal of Neuroscience*, 2001, 21(16), 6423–6429.

Rawson, N. E. et al., "The potential for retinoic acid (RA) to promote in the olfactory system" *Brain Aging, Identifying Accelerators and Brakes, The $2^{nd}$ Neurobiology of Aging Conference*, Nov. 8–9, 2001, Delegate Manual.

Yee, K.K. et al., "Retinoic acid enhances the rate of recovery of olfactory function following nerve transection", *Amer. Chem. Soc.*, 2001, Abstracts 189.

* cited by examiner

METHODS OF TREATING ANOSMIA AND REPOPULATING OLFACTORY NERVES WITH RETINOIDS

CROSS-REFERENCE TO RELATED APPLICATIONS

This application claims priority to U.S. provisional application Ser. No. 60/237,900 filed Oct. 4, 2000, which is incorporated herein by reference in its entirety.

GOVERNMENT SUPPORT

This invention was supported by funds from the U.S. Government (National Institutes of Health Grant Nos. NIH 5 T32 DC00214, DC0004645, and DC0002876) and the U.S. Government may therefore have certain rights in the invention.

FIELD OF THE INVENTION

The present invention is directed, in part, to novel methods of treating complicated anosmia in a mammal, to methods of enhancing the rate of olfactory nerve recovery in a mammal, and to methods of enhancing nerve regeneration in a mammal.

BACKGROUND OF THE INVENTION

Injuries to the central nervous system (CNS), such as, for example, stroke, chronic nasal sinus disease, allergic rhinitis, neurodegenerative disease, head trauma, viral or bacterial infection, and surgery, can result in olfactory dysfunction, which affects nearly three million Americans. A complete loss of smell is referred to as "anosmia" whereas a decrease in smell sensitivity is referred to as "hyposmia." Unfortunately, there is little that can be done to cure or treat the condition effectively. Further, recovery from head trauma can take many months or even years and is often incomplete even after apparent physical recovery.

The ability of the olfactory system to replace degenerating olfactory neurons caused by age or injury has been examined. Morphological studies have demonstrated degeneration of mature olfactory neurons in the olfactory epithelium after axotomy, followed by an increase in the proliferation of basal cells. Cancalon et al., *J. Cell Biol.*, 1980, 84, 779–794; Graziadei et al., *J. Cell Biol.*, 1973, 59, 525–30; Graziadei and Monti Graziadei, The olfactory system: a model for the study of neurogenesis and axon regeneration in mammals. In: C. W. Cotman (Ed.), Neuronal Plasticity, New York, Raven Press, 1978, pp. 131–153; Oley et al, *J. Comp. Physiol. Psychol*, 1975, 88, 477–495; and Simmons et al., *J. Neurophysiol.*, 1981, 45, 529–549. With time, the basal cells differentiate into olfactory neurons that can connect to the olfactory bulb and restore function. Costanzo, *Brain. Res.*, 1985, 361, 258–266 and Yee et al., *Physiol. Behav.*, 1995, 58, 959–968. Few studies, however, have examined possible ways to improve recovery after denervation. The time for some recovery of behavioral function varies with species; in hamsters, for example, recovery occurs in approximately 20 days. Anatomical recovery is reported to take about 30 days in most species studied. Cummings et al., *J. Comp. Neurol.*, 2000, 421, 362–373; Monti Graziadei et al., *J. Neurocytol.*, 1979, 8, 197–213; Graziadei and Monti Grazaiadei, The olfactory system: a model for the study of neurogenesis and axon regeneration in mammals. In: C. W. Cotman (Ed.), Neuronal Plasticity, New York, Raven Press, 1978, pp.131–153. Within the central nervous system, it is thought that minimal regeneration occurs, except for a population of stem cells within the subventricular zone that proliferate and are thought to contribute to cell repopulation in the olfactory bulb. Gheusi et al., *Proc. Natl. Acad. Sci. USA*, 2000, 97, 1823–1828.

Vitamin A has been used to treat uncomplicated anosmia but was found not to be useful in treating anosmia associated with skull injuries and fractures with sheering of olfactory nerves, i.e., complicated anosmia. Duncan et al., *Archives of Otolaryngology*, 1962, 75, 116–124. Recent evidence has demonstrated that retinoic acid (RA), a metabolite of vitamin A, plays an important role in the development and morphogenesis of the fetal olfactory system. Anchan et al., *J. Comp. Neurol.*, 1997, 379, 171–184; LaMantia et al., *Neuron*, 1993, 10, 1035–1048; and Simmons et al., *J. Neurophysiol.*, 1981, 45, 529–549. There is also evidence that RA plays a role in the growth of the adult olfactory system. Gustafson et al., *Dev. Brain Res.*, 1999, 114, 121–126; Whitesides et al., *J. Comp. Neurol.*, 1998, 394, 445–461; Zhang, *Biochem. Biophys. Res. Commun.*, 1999, 256, 346–351; and Corcoran et al., *Nat. Neurosci.*, 1999, 2, 307–308. Vitamin A has been postulated to have an effect on mRNA expression levels of olfactory marker protein (Aderoju et al., *Amer. Chem. Soc. Abstracts*, 2000, Abstract 193) and gene expression in neurons in vivo (Asson-Barres et al., *Amer. Chem. Soc. Abstracts*, 2000, Abstract 195). In addition, retinoic acid has been postulated to play a role in olfactory epithelium via retinoic acid binding proteins (Ahmad et al., *Amer. Chem. Soc. Abstracts*, 2000, Abstract 194). Thus, methods of treating complicated anosmia in mammals, enhancing the rate of olfactory nerve recovery in mammals, and enhancing nerve regeneration in mammals is greatly needed.

SUMMARY OF THE INVENTION

The present invention is directed to, inter alia, methods of treating complicated anosmia in a mammal comprising administering an effective amount of a retinoid compound to the mammal.

The present invention is also directed to methods of enhancing the rate of olfactory nerve recovery in a mammal after injury comprising administering an effective amount of a retinoid compound to the mammal.

The present invention is also directed to methods of enhancing nerve regeneration in a mammal comprising administering an effective amount of a retinoid compound to the mammal.

DETAILED DESCRIPTION OF PREFERRED EMBODIMENTS

Figure 1:
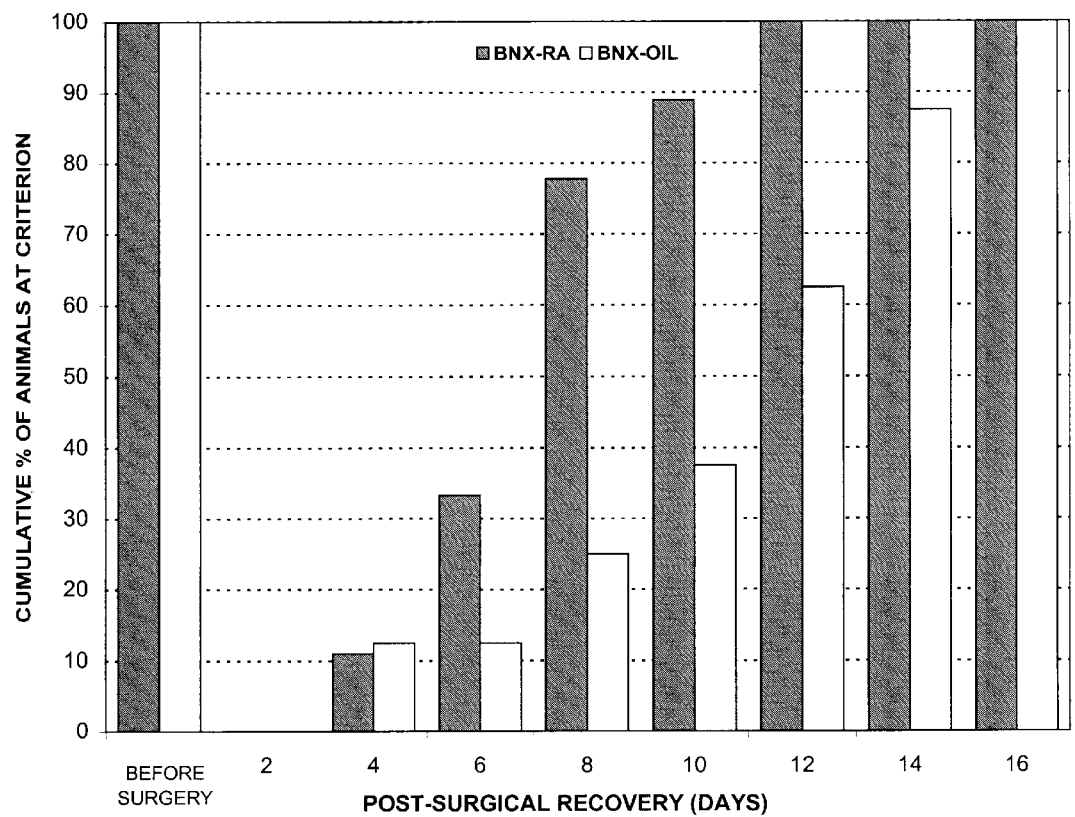
FIG. 1 is a graph showing representative training and recovery curves for mice which have undergone bilateral olfactory nerve transection (BNX) compared to sham groups from pre-surgical day −5 to post-surgical day 14. All animals were able to find the buried food in ≦30 seconds before surgery (day 0, vertical line). After surgery, all the BNX animals were unable to find the buried food within 180 seconds whereas the sham-RA (■) and sham-oil (□) groups performed at pre-surgical levels. With time, all animals recovered. The initial rate of recovery, however, was faster for the BNX-RA (●) than for BNX-oil (○) groups. Data points represent the mean food-finding times (sec)±SEM.

Applicants have discovered that RA can be used to treat complicated anosmia in mammals, enhance the rate of olfactory nerve recovery in mammals, and enhance nerve regeneration in mammals by administering an effective amount of a retinoid compound to the mammal.

Various definitions are made throughout this document. Most words have the meaning that would be attributed to those words by one skilled in the art. Words specifically defined either below or elsewhere in this document have the meaning provided in the context of invention as a whole and as are typically understood by those skilled in the art.

As used herein, the term "about" means ±10% of the value it modifies.

The present invention is directed to methods of using a retinoid compound in vivo in mammals. One embodiment of the invention is directed to a method of treating complicated anosmia in a mammal comprising administering an effective amount of a retinoid compound to the mammal. Complicated anosmia is associated with sheering of olfactory nerves often caused by skull injuries such as skull fractures. An effective amount of a retinoid compound is an amount that provides an increase in the sensation of smell, such as any improvement in the ability to perceive, identify or discriminate smells.

Another embodiment of the invention is directed to a method of enhancing the rate of olfactory nerve recovery in a mammal after injury comprising administering an effective amount of a retinoid compound to the mammal. Injury includes, but is not limited to, damage caused by or as a result of bilateral olfactory nerve transection, head trauma, chronic nasal sinus disease, allergic rhinitis, viral infection, bacterial infection, stroke, neurodegenerative disorder, surgery, and the like. An effective amount of a retinoid compound is an amount that provides an increase in the rate or completeness of olfactory nerve recovery. The rate of recovery can be measured by, for example, comparing the length of time required to regain or recover the sensation of smell compared to an untreated mammal. In addition, recovery can also be measured by testing an animal's ability to discriminate, identify, rate the intensity of, associate a task with, avoid or prefer a smell. The retinoic acid compound is preferably administered immediately after injury but can also be administered hours, days or even weeks after injury. The retinoic acid is preferably administered immediately after or up to 2 days after injury. Alternately, the retinoid compound can be administered to the mammal prior to injury in circumstances where risk of injury is known or expected.

Another embodiment of the invention is directed to a method of enhancing nerve cell (neuron) replacement following injury in a mammal comprising administering an effective amount of a retinoid compound to the mammal. An effective amount of a retinoid compound is an amount that provides an increase in nerve cell repopulation, i.e., new cells or regeneration of existing cells. An increase in nerve repopulation can be determined by, for example, macroscopic examination, magnetic resonance imaging, and similar techniques, or can be determined by observing an increase in the activity of the nerve or the behavior mediated by nerves. Preferably, the nerve is a part of the central nervous system, more preferably an olfactory neuron.

Retinoid compounds include, but are not limited to, compounds having the following structure of retinoic acid,

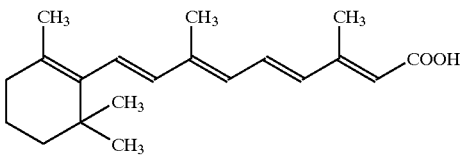

or pharmaceutical salts thereof, derivatives having a structure similar to that of retinoic acid, as well as biologically equivalent derivatives thereof. Retinoic acid derivatives include, but are not limited to, natural and synthetic compounds having biochemically equivalent moieties bound to the carboxylic carbon atom. Typical salts are the alkalimetal and ammonium salts. Preferred salts of the acid include, but are not limited to, sodium, potassium, and ammonium salts. In addition, retinoid compounds include, but are not limited to, retinol, 9-cis-retinol, didehydroretinol, 13-cis-retinoic acid, 13-trans-retinoic acid, all-trans retinoic acid, didehydroretinoic acid, retinaldehyde, analogs thereof, and the like. In addition, any combination of two or more retinoid compounds can also be used in the present invention. Retinoic acid receptor-specific and function-specific ligands are also described in Thacher et al., Curr. Pharm. Design, 2000, 6 25–58, which is incorporated herein by reference in its entirety.

Mammals include, but are not limited to, rodents (rat, mouse, hamster, etc.), dogs, cats, horses, and humans.

An effective amount of a retinoid compound is preferably from about 100 µg/kg to about 1 g/kg, more preferably from about 500 µg/kg to about 500 mg/kg, more preferably from about 750 µg/kg to about 250 mg/kg, more preferably from about 1 mg/kg to about 75 mg/kg, and most preferably about 2.5 mg/kg. One skilled in the art can readily adjust dosages based upon desired and obtained results. Optimal dosages and routes of administration will depend, of course, on the age, weight, injury, and species of mammal, pharmacodynamic characteristics of the particular agent, and its mode and route of administration, and the nature and extent of symptoms, kind of concurrent treatment, frequency of treatment, and the effect desired.

The retinoid compound can be administered to the mammal by a number of routes including, but not limited to, oral, intranasal, intramuscular, intraperitoneal, intradermal, subcutaneous, intravenous, intraarterial, intraoccular, transdermal or by suppository. Preferred routes of administration include oral, nasal, and by injection.

One having ordinary skill in the art can readily formulate a pharmaceutical composition that comprises a retinoid compound. An effective amount of a retinoid compound can be formulated according to the mode of administration to be used. The compositions can be conveniently administered in unit dosage form and can be prepared by any of the methods well known in the pharmaceutical art, for example, as described in Remington's Pharmaceutical Sciences (Mack Pub. Co., Easton, Pa., 1980), the disclosure of which is incorporated herein by reference in its entirety. The retinoid compound can be formulated, for example, as a solution, suspension, emulsion or lyophilized powder in association with a pharmaceutically acceptable carrier. Examples of such carriers are water, saline, Ringer's solution, dextrose solution, 5% human serum albumin, sesame oil, electrolytes/dextrose, fatty oils of vegetable origin, fatty esters, polyols, such as propylene glycol and polyethylene glycol, and the like. The composition can contain additives that maintain isotonicity (e.g., sodium chloride and mannitol) and chemical stability (e.g., buffers and preservatives). The formulation is sterilized by commonly used techniques and is preferably free of pyrogens.

The invention is further illustrated by way of the following examples which are intended to elucidate the invention. These examples are not intended, nor are they to be construed, as limiting the scope of the disclosure.

EXAMPLES

Example 1

Olfactory nerves can be lesioned to produce anosmia in adult hamsters. Yee et al., *Physiol. Behav.*, 1995, 58, 959–968. Unlike chemical exposures using zinc sulfate (Harding et al., *Brain Res.*, 1978, 140, 271–285) or methyl bromide (Youngentob et al., *Physiol. Behav.*, 1997, 62, 241–1252) and toxins like 3-methylindole (Setzer et al., *Physiol. Behav.*, 1998, 65, 489–96) or colchicine (Suzuki et al., *Anat. Embryol. (Berl)*, 1998, 198, 43–51), degeneration after olfactory nerve transection is specific to mature olfactory neurons and results in a transient, complete loss of smell. This type of damage is considered to be analogous to head trauma, in which the movement of the brain inside the skull causes trauma to the olfactory nerves which are vulnerable where they travel through small perforations in the cribriform plate.

Twenty-five adult male mice (CBA/J) ranging in age from 2–3 months were purchased from Jackson Laboratory (Bar Harbor, Me.). Two days prior to training and for the duration of the experiment, animals were placed on a limited food schedule of 1.5 g/day cheese-peanut butter crackers (Austin Quality Foods, Inc., Cary, N.C.) and 1–1.5 g of rodent chow (Purina 5001) with water ad libitum. The addition of 1–1.5 gm of chow (22–33 IU/day) is sufficient to maintain the daily-recommended requirement for vitamin A (1.1–2.0 IU) in a typical 25 g laboratory mouse. Hoag et al, In: Biology of the laboratory mouse, E. L. Green (Ed.), Dover Publications Inc, New York, 2000, pp. 39–43. Only animals that maintained body weights within 15% of initial weights were used.

A buried food task was used because of its efficiency and simplicity in determining whether animals can detect odorants after surgery and when olfactory function returns. Animals were trained to find a piece of cheese cracker randomly buried under approximately ½ inch of Aspen shavings. The time it took the animal to find and eat the piece of food was measured with a stopwatch. Animals were trained daily on 5 trials/day, with each trial lasting 180 seconds. The animal was removed from the test cage after eating the food or after 180 seconds.

After at least 5 days of performing at ≦30 seconds mean finding time, the animals were divided into two groups: a bilateral olfactory nerve transection (BNX) group and a surgical sham group. One day after surgery, animals were tested on two trials to determine the completeness of the nerve transection. The BNX animals that could not find the buried food (i.e., they were anosmic) received orally a single 0.1 ml administration of all-trans RA (atRA, 75 mg/kg) in sesame oil (BNX-RA, n=9) or 0.1 ml of sesame oil alone (BNX-oil, n=8). Sham animals were also tested and received either atRA (sham-RA, n=4) or oil (sham-oil, n=4). A similar treatment of normal animals without injury was shown previously to activate RA-sensitive gene expression in the olfactory epithelium of adult mice. Whitesides et al., *J. Comp. Neurol.*, 1998, 394, 445–461. Daily behavioral testing resumed the next day until recovery reached pre-surgical levels for 7 consecutive days or after 28 post-surgical days. Identities of the treatments were unknown to the investigator throughout post-surgical testing.

Animals receiving the BNX procedure were anesthetized with sodium pentobarbital (60 mg/kg, ip). In addition, halothane (0.5–2.0%) mixed with oxygen was used as an anesthetic inhalant during surgery. A flexible custom-made Teflon™ blade was inserted between the cribriform plate and olfactory bulb and then guided around the bulb, transecting the olfactory axons projecting across the cribriform plate. Identical procedures were done to both bulbs. Sham animals received similar surgical treatments except olfactory nerves were not transected. Details of the olfactory nerve transection procedure have been described previously. Yee et al., *Physiol. Behav.*, 1995, 58, 959–968.

FIG. 1 depicts the training and recovery curves from pre-surgical day −5 to post-surgical day 14. Longer recovery times are not shown because the data do not include all the animals. Before surgery (day 0), all the animals were able to find the buried food in ≦30 seconds. One day after surgery, all the BNX animals were unable to find the buried food within 180 seconds, demonstrating the effectiveness of the nerve transection to produce anosmia, whereas all the sham animals were able to find the buried food. The performance levels of both sham groups after surgery were similar to pre-surgical levels except on post-surgical day 2. The increase in the food-finding times suggests that the surgery and/or anesthetic might have had an effect on the level of performance. Food-finding times, however, returned to pre-surgical levels by the next day.

There was a significant difference in the recovery between the two BNX groups. A two-factor ANOVA repeated measures analysis (SPSS Inc., Chicago, Ill.) was used to determine the effects of RA on recovery from post-surgical days 3–14. Post-surgical day 2 was not included in the analysis since the BNX animals in both groups performed at 180 seconds. There was a significant treatment effect on mean food finding times across the recovery period ($F(1,15)=5.85$, $p<0.05$). There was also a significant treatment X day interaction ($F(11,165)=2.69$, $p<0.005$), indicating an effect on the rate of recovery.

Figure 2:
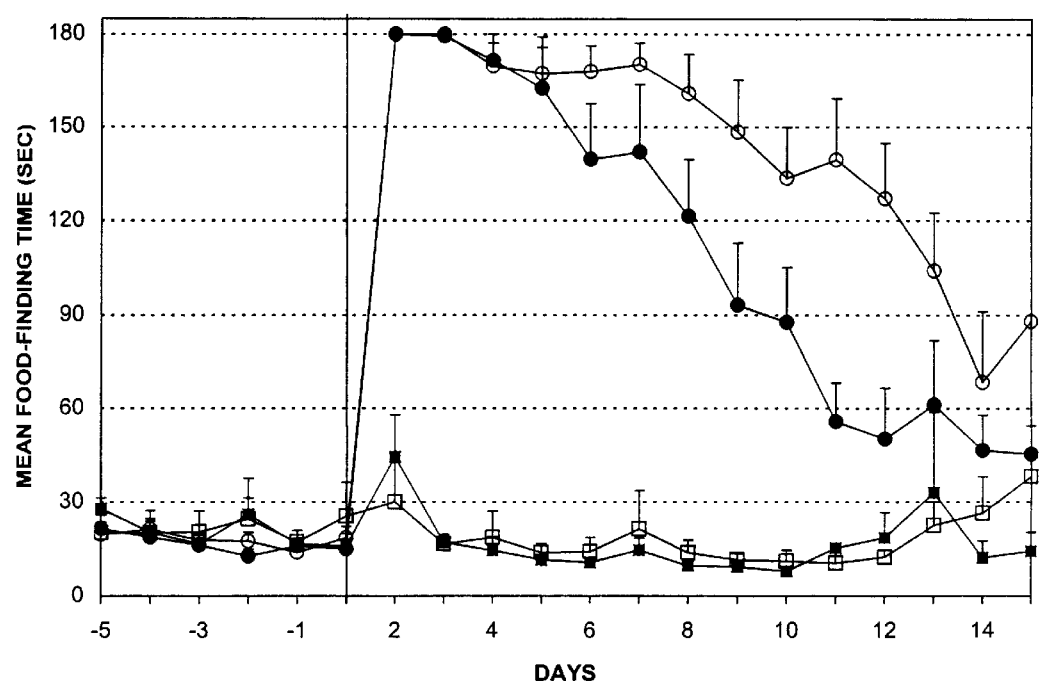
FIG. 2 is a graph showing representative cumulative percentage of BNX-RA (hatched bars) and BNX-oil (open bars) animals reaching criterion for initial recovery during post-surgical recovery days 2–16. Criterion is defined as the first day of three consecutive days on which the animal found the food in <180 seconds.

FIG. 2 depicts the cumulative percentage of animals that reached criterion for initial recovery (defined as the first day of three consecutive days of <180 seconds of food-finding time). Day 0 represents the test session before surgery when all the animals were able to find the food in ≦30 seconds (pre-surgical level). The BNX-RA animals reached criterion between post-surgical days 4–11 with a mean at post-surgical day 7.56±0.67. Similarly, the BNX-oil animals reached criterion between post-surgical days 4–15. The majority of these animals, however, reached criterion at a later post-surgical day of 10.75±1.28 ($F(1,15)=5.24$, $p<0.05$). There was no difference in the amount of recovery time needed for BNX-RA animals (9.8 days) and BNX-oil animals (9.25 days) to return to their pre-surgical level of performance (≦30 seconds; $F(1,15)=0.096$, $p=0.761$).

Although BNX-RA animals began to recover earlier than BNX-oil animals, both groups had a similar range for reaching criterion between post-surgical days 4–15. The nerve transection procedure involves the manipulation of the blade around the olfactory bulbs, which can lead to damage to the bulbs and the formation of scar tissue. Butler et al., *Neurosci. Lett.*, 1984, 48, 247–254. Both of these complications can decrease the amount of new axonal innervation and sensory information to the bulbs and delay the recovery of olfactory functions. It is possible that the BNX-RA treated animals had less damage to their olfactory bulbs or less amount of scar tissue than the BNX-oil animals. The treatments, however, were randomly given and the surgical conditions of the BNX animals were unknown to the investigator administering the treatment. Hence, it is unlikely that out of the 17 BNX animals, only those with the least amount of damage or scar formation were given RA. It is also possible that the rate of improvement in olfactory recovery may be due to the effects of RA on other aspects of functional recovery such as learning. Chiang et al., *Neuron*, 1999, 21, 1353–1361. The mean food-finding times after surgery, however, were similar for both sham groups. In addition, the number of recovery days needed to return to the pre-surgical level of performance was similar for both BNX groups.

As those skilled in the art will appreciate, numerous changes and modifications may be made to the preferred embodiments of the invention without departing from the spirit of the invention. It is intended that all such variations fall within the scope of the invention. The entire disclosure of each publication cited herein is hereby incorporated by reference.

What is claimed is:

1. A method of treating complicated anosmia in a mammal comprising administering an effective amount of a retinoid compound to said mammal wherein complicated anosmia is associated with sheering of olfactory nerves.

2. The method of claim 1 wherein said retinoid compound is retinoic acid.

3. The method of claim 1 wherein said retinoid compound is administered to said mammal orally, intranasally or by injection.

4. The method of claim 1 wherein said effective amount is from about 1 mg/kg to about 75 mg/kg.

5. The method of claim 1 wherein said mammal is a human.

6. A method of enhancing the rate of olfactory nerve recovery in a mammal after injury comprising administering an effective amount of a retinoid compound to said mammal.

7. The method of claim 6 wherein said retinoid compound is retinoic acid.

8. The method of claim 6 wherein said retinoid compound is administered to said mammal orally, intranasally or by injection.

9. The method of claim 6 wherein said effective amount is from about 1 mg/kg to about 75 mg/kg.

10. The method of claim 6 wherein said injury is head trauma, nasal sinus disease, allergic rhinitis, viral infection, bacterial infection, stroke, neurodegenerative disease, or surgery.

11. The method of claim 6 wherein said mammal is a human.

12. A method of enhancing nerve regeneration in a mammal following injury comprising administering an effective amount of a retinoid compound to said mammal wherein said injury is head trauma, nasal sinus disease, allergic rhinitis, viral infection, bacterial infection, stroke, neurodegenerative disease or surgery.

13. The method of claim 12 wherein said retinoid compound is retinoic acid.

14. The method of claim 12 wherein said retinoid compound is administered to said mammal orally, intranasally or by injection.

15. The method of claim 12 wherein said effective amount is from about 1 mg/kg to about 75 mg/kg.

16. The method of claim 12 wherein said mammal is a human.

17. The method of claim 12 wherein said nerve is an olfactory nerve.

\* \* \* \* \*